United States Patent [19]
Ue et al.

[11] Patent Number: 5,856,513
[45] Date of Patent: Jan. 5, 1999

[54] PROCESS FOR THE PREPARATION OF N-ALKYL-N'-METHYLIMIDAZOLINIUM SALT OF ORGANIC ACID

[75] Inventors: Makoto Ue; Masayuki Takeda; Takako Takahashi; Masahiro Takehara, all of Ibaraki, Japan

[73] Assignee: Mitsubishi Chemical Corporation, Tokyo, Japan

[21] Appl. No.: 888,196

[22] Filed: Jul. 3, 1997

[30] Foreign Application Priority Data

Jul. 4, 1996 [JP] Japan ................................. 8-174895

[51] Int. Cl.$^6$ ...................... C07D 233/04; C07D 233/56; C07D 233/06; C07D 233/08
[52] U.S. Cl. ...................... 548/347.1; 540/335.1
[58] Field of Search ............... 548/335.1, 347.1

[56] References Cited

U.S. PATENT DOCUMENTS

| | | | |
|---|---|---|---|
| 2,493,318 | 1/1950 | Shonle et al. | 548/335.1 |
| 2,891,025 | 6/1959 | Price | 548/335.1 X |
| 3,121,091 | 2/1964 | Green | 548/335.1 X |
| 3,236,881 | 2/1966 | Distler et al. | 548/335.1 X |
| 3,723,512 | 3/1973 | Niederprum et al. | 548/335.1 X |
| 4,542,214 | 9/1985 | Bechara | 548/335.1 X |
| 4,841,066 | 6/1989 | Goertz et al. | 548/335.1 |
| 5,001,156 | 3/1991 | Philippe et al. | 514/555 |
| 5,683,832 | 11/1997 | Bonhote et al. | 429/111 |

FOREIGN PATENT DOCUMENTS

| | | | |
|---|---|---|---|
| 1519132 | 2/1968 | France | 548/335.1 |
| 0626475 | 7/1949 | United Kingdom | 548/335.1 |
| 91/14678 | 10/1991 | WIPO | 548/335.1 |

*Primary Examiner*—Floyd D. Higel
*Attorney, Agent, or Firm*—Oblon, Spivak, McClelland, Maier & Neustadt, P.C.

[57] ABSTRACT

An N-alkyl-N'-methylimidazolinium salt of an organic acid is prepared in high purity and in high yield by (a) preparing an N-alkyl-N'-methylimidazolinium methyl carbonate in a quaternization reaction by methylating an N-alkylimidazoline with dimethyl carbonate and (b) reacting the resulting N-alkyl-N'-methylimidazolinium methyl carbonate with an organic acid, in an anion exchange reaction, wherein the reaction of each step is conducted in methanol solvent.

15 Claims, 3 Drawing Sheets

PROCESS FOR THE PREPARATION OF N-ALKYL-N'-METHYLIMIDAZOLINIUM SALT OF ORGANIC ACID

FIELD OF THE INVENTION

This invention relates to a process for preparing, in a high yield and at a high purity, a useful N-alkyl-N'-methylimidazolinium salt of an organic acid which is used in a wide range of fields as a surfactant (shampoo base, fiber softener, antistatic agent, static charge regulator or the like), a chemical for ink-jet printing paper, an electrolyte for electrochemical devices, a catalyst for curing of a resin or a phase transfer catalyst.

BACKGROUND OF THE INVENTION

Three conventional processes are primarily known for synthesizing a quaternary ammonium salt of an organic acid. They are as follows:

(1) Preparing a quaternary ammonium salt of an organic acid by reacting a halogenated quaternary ammonium salt, which has been synthesized by a quaternizing reaction of a tertiary amine with an alkyl halide, with a metal salt of an organic acid in a solvent, and then removing the insoluble halogenated metal salt JP-A-63-8359 ("JP-A" as used herein means an "unexamined published Japanese patent application").

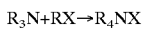

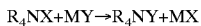

(2) Preparing a quaternary ammonium salt of an organic acid by first synthesizing a quaternary ammonium hydroxide by subjecting a halogenated quaternary ammonium salt, which has been synthesized through a quaternizing reaction of a tertiary amine with an alkyl halide, to form a quaternary ammonium hydroxide by electrolysis (JP-B-45-28564; "JP-B" means an "examined Japanese patent publication"), by ion exchange resin (JP-A-52-3009), by the silver oxide method (R. C. Peterson et al., J. Amer. Chem. Soc., 1959, 81, 3264) or the like, and then neutralizing the resulting ammonium salt with an organic acid.

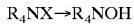

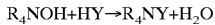

(3) Preparing a quaternary ammonium salt of an organic acid by reacting a quaternary ammonium carbonate, which has been synthesized by quaternizing a tertiary amine with a carbonate diester, with an organic acid and then subjecting the reaction mixture to decarboxylation (JP-A-63-280045).

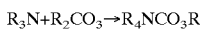

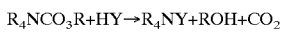

In the first process (1) described above, a quaternary ammonium salt is separated by making use of the difference in the solubility between the quaternary ammonium salt of an organic acid and a metal halide salt. This method is accompanied with the drawback that the metal halide salt cannot be removed from the reaction mixture completely so that only a low-purity quaternary ammonium salt of an organic acid can be obtained.

The second process (2) described above, which employs a quaternary ammonium hydroxide is one of the most commonly used synthesis processes. For industrial preparation, this process is carried out by the electrolysis method. However, preparation of a high-purity product having impurity contents which are on the order of ppm is costly. For preparation on the laboratory scale, the ion exchange resin method or silver oxide method is normally used. However, both of these techniques present problems in purity similar to the process (1) described above.

Process (3) is the most advantageous process of the three processes. However, from the viewpoint of the purity of the quaternary ammonium salt, the process requires high-temperature and high-pressure reaction conditions.

For the preparation of an N-alkyl-N'-methylimidazolinium salt of an organic acid by using an N-alkylimidazoline as a tertiary amine and adopting the above-described synthesis of a quaternary ammonium salt of an organic acid, neither process (1) nor process (2) can be employed, because the former cannot provide a high purity product and the latter does not permit the stable existence of a hydroxide of an N-alkyl-N'-methylimidazolinium (B. Fernandez et al., J. C. S. Perkin II; 1978, 545).

According to process (3), it is impossible to obtain a high-purity N-alkyl-N'-methylimidazolinium salt of an organic acid in a high yield, because, different from the conventionally-employed tetraalkylammonium methyl carbonate, N-alkyl-N'-methylimidazolinium methyl carbonate formed in the quaternizing reaction step cannot be isolated because of its thermal instability and moreover it inevitably undergoes decomposition prior to reaction with an organic acid.

Furthermore, since an N-alkylimidazoline as the raw material and N-alkyl-N'-methylimidazolinium methyl carbonate are unstable to water and undergo hydrolysis as shown in Formulae (2) and (3), respectively, it is impossible to obtain a high-purity N-alkyl-N'-methylimidazolinium salt of an organic acid in a high yield.

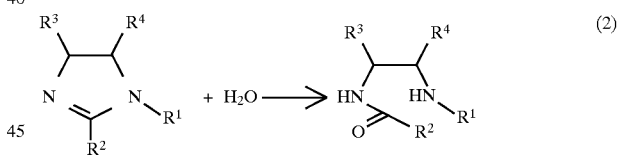

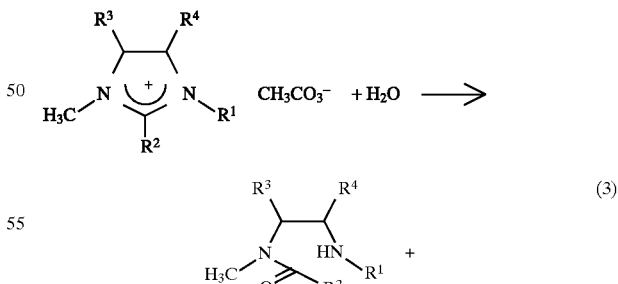

In the above-described processes for producing an N-alkyl-N'-methylimidazolinium salt of an organic acid, N-alkyl-N'-methylimidazolinium methyl carbonate, which is formed in the quaternizing reaction step, is thermally unstable and is prone to undergo hydrolysis. It is impossible to apply the conventional process for the preparation of a quaternary ammonium salt of an organic acid as disclosed in JP-A-63-280045 without any modification. A need, therefore, continues to exist for a process of preparing an N-alkyl-N'-methylimidazolinium salt of an organic acid in high yield and high purity.

SUMMARY OF THE INVENTION

Accordingly, one object of the present invention is to provide a process for the preparation of a high-purity N-alkyl-N'-methylimidazolinium salt of an organic acid in high yield.

Briefly, this object and other objects of the invention as hereinafter will become more readily apparent can be attained by a process for the preparation of an N-alkyl-N'-methylimidazolinium salt of an organic acid, which comprises (a) preparing an N-alkyl-N'-methylimidazolinium methyl carbonate by methylating an N-alkylimidazoline with dimethyl carbonate and (b) reacting the resulting N-alkyl-N'-methylimidazolinium methyl carbonate with an organic acid in an anion exchange reaction, wherein methanol is used as a reaction solvent for both steps (a) and (b).

The use of methanol as a solvent in both steps (a) and (b) stabilizes the N-alkyl-N'-methylimidazolinium methyl carbonate, which is an intermediate, and makes it possible to provide an N-alkyl-N'-methylimidazolinium salt of an organic acid at high purity in a higher yield.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
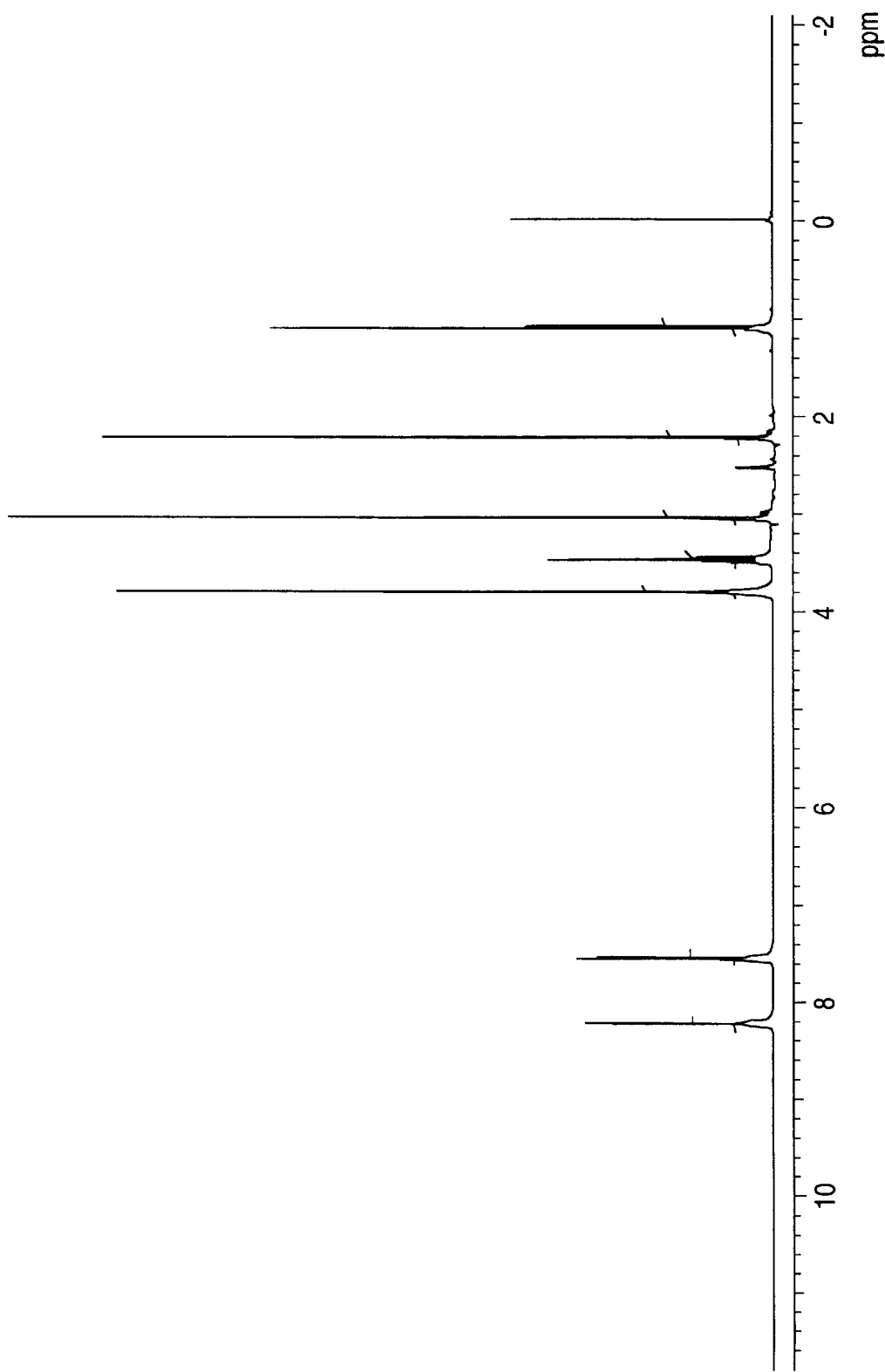
FIG. 1 illustrates an $^1$H-NMR chart of 1-ethyl-2,3-dimethylimidazolinium hydrogen phthalate in dimethyl sulfoxide-$d_6$.

The present invention is described specifically as follows:

Step (a):

Step (a) is a quaternization reaction step which produces the imidazolinium methyl carbonate salt of formula (4):

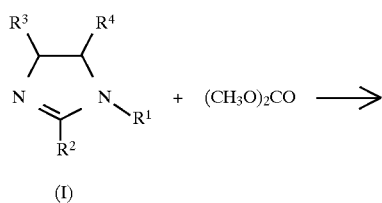

-continued

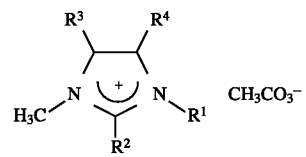

wherein $R^1$ represents a $C_{1-4}$ alkyl group, $R^2$ represents a $C_{1-19}$ alkyl group or a hydrogen atom, $R^3$ and $R^4$ each independently represents a methyl group, an ethyl group or a hydrogen atom, in which N-alkyl-N'-methylimidazolinium methyl carbonate is prepared by methylating an N-alkylimidazoline represented by the formula (I) with dimethyl carbonate in a methanol solvent.

In step (a), an N-alkylimidazoline, dimethyl carbonate and a methanol solvent are charged into a pressure reactor. After the reactor is purged with nitrogen gas, the reaction is conducted. Dimethyl carbonate is added in an amount of 1 to 5 moles, preferably 1 to 2 moles and more preferably 1.3 to 1.7 moles per mole of the N-alkylimidazoline. The methanol solvent, on the other hand, is added in an amount of 1 to 20 moles, preferably 2 to 10 moles, more preferably 3 to 7 moles per mole of the N-alkylimidazoline. The reaction temperature is 110° to 170° C., with 130° to 150° C. being preferred. Under the above conditions, the reaction pressure ranges from 5 to 20 atmospheres pressure. The reaction time differs with the reaction temperature or the composition charged but ranges from about 2 to 24 hours.

The N-alkyl-N'-methylimidazolinium methyl carbonate formed in step (a) is not stable and inevitably undergoes decomposition when it exists alone. The methanol solvent has stabilizing effects of the N-alkyl-N'-methylimidazolinium methyl carbonate through hydrogen bonding. When an aprotic solvent is used as a reaction solvent, it does not bring about stabilizing effects through hydrogen bonding so that the N-alkyl-N'-methylimidazolinium methyl carbonate tends to undergo decomposition, resulting in a marked reduction in its yield. Protic solvents such as ethanol or isopropanol also have stabilizing effects on the N-alkyl-N'-methyliidazolinium methyl carbonate, but they produce complicated by-products because of the interesterification reaction between dimethyl carbonate and an alcohol, resulting in a reaction yield inferior to the case where methanol is used as a solvent.

The raw material N-alkylimidazoline and the product N-alkyl-N'-methylimidazolinium methyl carbonate undergo hydrolysis quantitatively and provide by-products having formulae (2) and (3) above so that it is necessary to keep the internal state of the reaction system water-free. The raw material and solvent ordinarily contain trace amounts of water as impurities. Accordingly, they are treated with a dehydrating agent such as a molecular sieve in order to remove water as much as possible and then purified by distillation or the like. The water content as small as possible is preferred. If the water content in the system is maintained at less than 1 wt. %, in practice, an N-alkyl-N'-methylimidazolinium salt of an organic acid having sufficiently high purity can be obtained.

Suitable examples of the N-alkylimidazoline raw material of this invention (represented by the formula (I)) include 1-methylimidazoline, 1-ethylimidazoline 1,2-dimethylimidazoline, 1-ethyl-2-methylimidazoline, 1,2,4-trimethylimidazoline, 1-ethyl-2,4-dimethylimidazoline, 1,4-dimethyl-2-ethylimidazoline and the like.

Step (b)

Step (b) is an anion exchange reaction step in which a quaternary ammonium salt of an organic acid is obtained by reacting the N-alkyl-N'-methylimidazolinium methyl carbonate, which has been obtained in step (a), with an organic acid in methanol solvent, followed by decarboxylation. The reaction step is as follows:

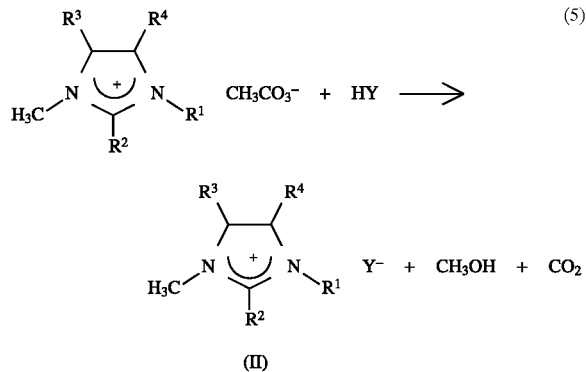

wherein $R^1$, $R^2$, $R^3$ and $R^4$ have the same meanings as defined in formula (I) and HY represents an organic acid.

As disclosed in JP-A-63-280045, when water is used as a reaction solvent, the N-alkyl-N'-methylimidazolinium methyl carbonate undergoes hydrolysis. It is therefore necessary to use a water-free organic solvent. The N-alkyl-N'-methylimidazolinium methyl carbonate cannot be isolated. Accordingly, a reaction solvent containing methanol in an amount sufficient enough to permit stabilization is required. Therefore, an N-alkyl-N'-methylimidazolinium methyl carbonate mixture containing methanol, the mixture being obtained by distilling off dimethyl carbonate (and excessive methanol) from the reaction mixture of step (a) under reduced pressure, is reacted with an organic acid in a suitable organic solvent. As the organic solvent, methanol is preferred from the viewpoint of the stability of the above-described N-alkyl-N'-methylimidazolinium methyl carbonate.

Methanol is used from the viewpoint of the stability of the N-alkyl-N'-methylimidazolinium methyl carbonate. In addition, the use of methanol is accompanied by the advantages that it can easily dissolve the N-alkyl-N'-methylimidazolinium methyl carbonate, an organic acid and the target N-alkyl-N'-methylimidazolinium salt of an organic acid and is readily removed by distillation after the completion of the reaction because of its low boiling point.

Methanol solvent is added in an amount of 1 to 20 moles, preferably 2 to 10 moles, more preferably 3 to 7 moles per mole of the N-alkyl-N'-methylimidazolinium methyl carbonate. The water content of methanol should be as small as possible. In practice, an N-alkyl-N'-methylimidazolinium salt of an organic acid having a sufficiently high purity can be obtained when the water content in the reaction system is maintained at less than 1 wt. %.

It is easier and more economical to employ the methanol, which has been used in step (a), as is as the reaction solvent for the step (b), and preferably the reaction mixture, which has been obtained in step (a), is used as is in step (b). At this time, even if methanol and unreacted dimethyl carbonate are present in the reaction mixture obtained in step (a), they do not exert adverse effects on the reaction in step (b) and are therefore not problematic.

It does not matter whether an organic acid is added to the reaction mixture obtained in step (a) or the reaction mixture obtained in step (a) is added to an organic acid. It is also possible to improve operability by adding a proper anhydrous organic solvent to an organic acid.

The reaction temperature is 10° to 100° C., with 20° to 60° C. being preferred. Since an endothermic reaction occurs because of the foaming of carbon dioxide gas, heating is required. In the case of an organic acid having a higher acidity than carbon dioxide, this reaction proceeds quantitatively and goes to completion at the time when the carbon dioxide gas stops foaming.

The solvent is then removed by distillation, followed by drying, whereby a high purity N-alkyl-N'-methylimidazolinium salt of an organic acid can be obtained in a high yield. It is also possible to carry out purification through recrystallization as needed, thereby increasing purity.

Suitable examples of the organic acid usable in the present invention include various carboxylic acids, sulfonic acid, alkyl phosphates and phenols. More specific examples include aliphatic monocarboxylic acids such as formic acid, acetic acid, propionic acid, butyric acid and trifluoroacetic acid; saturated aliphatic dicarboxylic acids such as oxalic acid, malonic acid, succinic acid, glutaric acid, adipic acid, pimelic acid, suberic acid, azelaic acid, sebacic acid, undecandioic acid, dodecandioic acid, tridecandioic acid, dimethylmaloic acid, diethylmaloic acid, dipropylmaloic acid, 2-methylglutaric acid, 3-methylglutaric acid, 3,3-dimethylglutaric acid, 3-methyladipic acid, 1,6-decanedicarboxylic acid, 5,6-decanedicarboxylic acid, 2,3-dibutylsuccinic acid and cyclohexanedicarboxylic acid; unsaturated aliphatic dicarboxylic acids such as maleic acid, citraconic acid, dimethylmaleic acid, and 1,2-cyclohexenedicarboxylic acid; aromatic monocarboxylic acids such as benzoic acid, toluic acid, cuminic acid, t-butylbenzoic acid, salicylic acid, γ-resorcylic acid and anisic acid; aromatic dicarboxylic acids such as phthalic acid, 4-methylphthalic acid and 4-nitrophthalic acid; sulfonic acids such as benzenesulfonic acid, p-toluenesulfonic acid, trifluoromethanesulfonic acid and nanofluorobutanesulfonic acid; alkyl phosphates such as monomethyl phosphate and dimethyl phosphate; phenols such as phenol, 2,4-dinitrophenol and picric acid; and nitrogen acids or carbon acids such as bis(trifluoromethanesulfonyl)imide and tris(trifluoromethanesulfonyl)methane. Among them, organic acids having high acidity are preferred from the standpoint of equilibrium, with phthalic acid and benzoic acid being particularly preferred.

The amount of the organic acid used may be adjusted so as to give a desired acid-base ratio, however, the organic acid should be added in an amount at least equivalent to the N-alkyl-N'-methylimidazolinium methyl carbonate obtained in the step (a). In general, an N-alkyl-N'-methylimidazolinium salt of an organic acid having an N-alkyl-N'-methylimidazolinium cation and a hydrogen phthalate anion or benzoate anions at a ratio of 1:1 is frequently employed.

EXAMPLE 1

Into a 100-ml autoclave, 16.8 g (0.15 mole) of 1-ethyl-2-methylimidazoline, 20.3 g (0.225 mole) of dimethyl carbonate and 19.2 g (0.60 mole) of methanol are charged. By a Karl Fischer determination, the water content in the system is 240 ppm. The autoclave is heated for about 30 minutes to 135° C., at which reaction is effected for 7 hours. As a result of an analysis of the reaction mixture by liquid chromatography, it is found that the conversion ratio of 1-ethyl-2-methylimidazoline is 100% and the yield of 1-ethyl-2,3-dimethylimidazolinium methyl carbonate is 98%.

When 24.9 g (0.15 mole) of phthalic acid is added to the reaction mixture, foaming due to the generation of a carbon dioxide gas is observed. From the reaction mixture, methanol and dimethyl carbonate are distilled off under reduced pressure, and 1-ethyl-2,3-dimethylimidazolinium hydrogen phthalate is obtained in a yield of 98%. The product so obtained is analyzed by liquid chromatography. As a result, it is found that the purity is 99.5% or higher and the melting point is 50° C.

Figure 2:
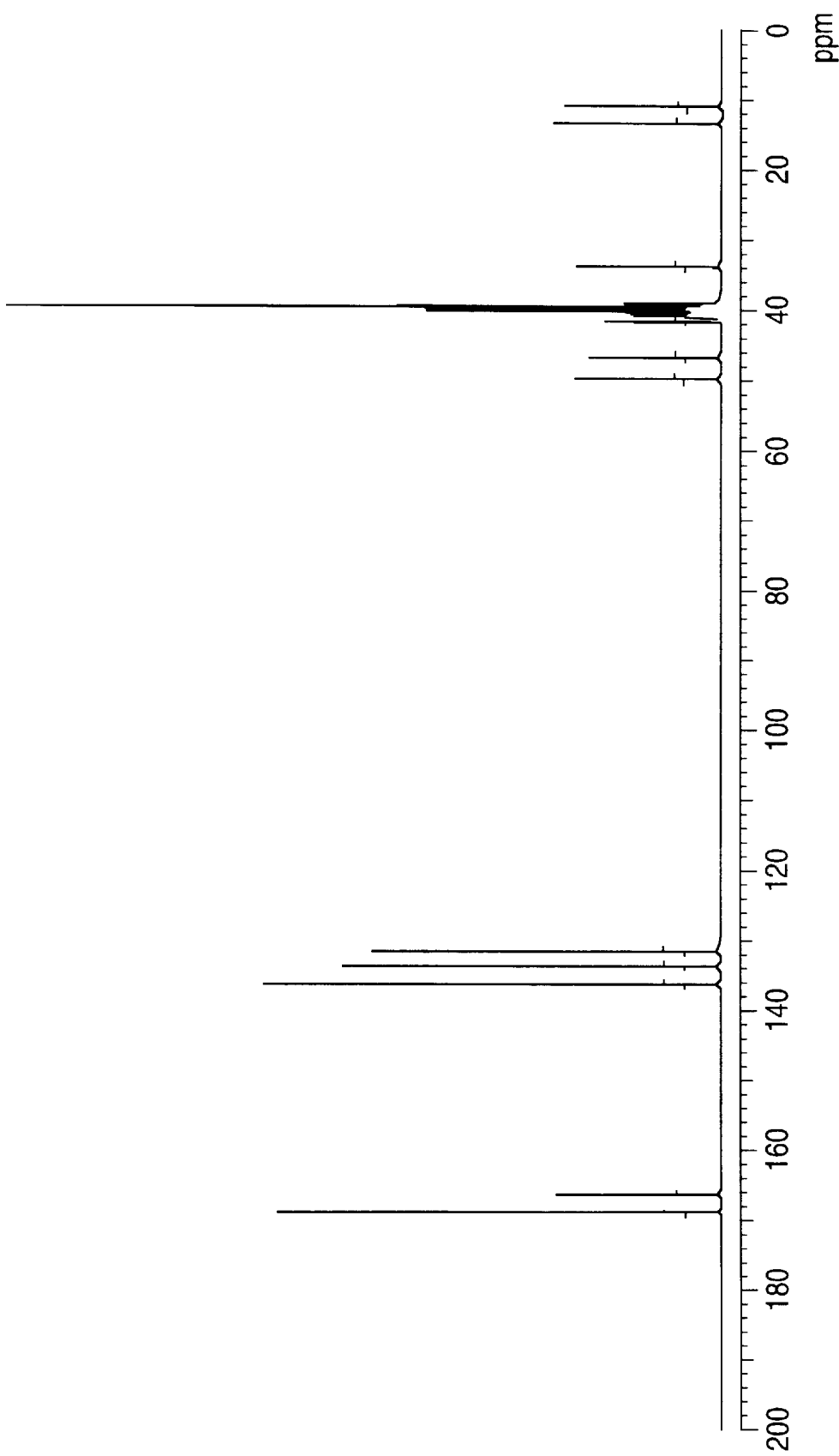
FIG. 2 illustrates a $^{13}$C-NMR chart of 1-ethyl-2,3-dimethylimidazolinium hydrogen phthalate in dimethyl sulfoxide-$d_6$.

The structure of the product is identified by elemental analysis, $^1$H-NMR (FIG. 1) and $^{13}$C-NMR (FIG. 2).

Found: C, 61.71; H, 6.98; N, 9.45. Calculated: C, 61.63; H, 6.90; N, 9.58

EXAMPLE 2

The procedure of Example 1 is conducted except that 14.7 g (0.15 mole) of 1,2-dimethylimidazoline is used instead of 1-ethyl-2-methylimidazoline. The results of the quaternizing reaction are shown in Table 1. The target 1,2,3-trimethylimidazolinium hydrogen phthalate is obtained in a yield of 98%. As a result of an analysis of the target product by liquid chromatography, it is found that the purity is 99.5% or higher and the melting point is 103° C. Incidentally, the structure of the product is identified by elemental analysis, $^1$H-NMR and $^{13}$C-NMR.

EXAMPLE 3

The procedure of Example 1 is conducted except that 1,2,4-trimethylimidazoline is used instead of 1-ethyl-2-methylimidazoline. The results of the quaternizing reaction are shown in Table 1. The target 1,2,3,4-tetramethylimidazolinium hydrogen phthalate is obtained in a yield of 98%. As a result of an analysis of the target product by liquid chromatography, it is found that the purity is 99.5% or higher. The product structure is identified by elemental analysis, $^1$H-NMR and $^{13}$C-NMR.

EXAMPLE 4

Into a 100-ml autoclave, 16.8 g (0.15 mole) of 1-ethyl-2-methylimidazoline, 20.3 g (0.225 mole) of dimethyl carbonate and 19.2 g (0.60 mole) of methanol are charged. By a Karl Fischer determination, the water content in the system is 500 ppm. The autoclave is heated over about 35 minutes to 145° C., at which temperature reaction is effected for 5 hours. As a result of an analysis of the reaction mixture by liquid chromatography, it is found that the conversion ratio of 1-ethyl-2-methylimidazoline is 100% and the yield of methyl carbonate 1-ethyl-2,3-dimethylimidazolinium is 98%.

When 18.3 g (0.15 mole) of benzoic acid are added to the reaction mixture, foaming due to the generation of carbon dioxide gas is recognized. From the reaction mixture, methanol and dimethyl carbonate are distilled off under reduced pressure, whereby 1-ethyl-2,3-dimethylimidazolinium benzoate is obtained in a yield of 98%. As a result of an analysis of the product so obtained by liquid chromatography, it is found that the purity is 99.5% or higher and the melting point is 98° C. The structure of the product is identified by elemental analysis, $^1$H-NMR and $^{13}$C-NMR.

EXAMPLE 5

The procedure of Example 4 is conducted except that 14.7 g (0.15 mole) of 1,2-dimethylimidazoline are used instead of 1-ethyl-2-methylimidazoline. The results of the quaternizing reaction are shown in Table 1. The target 1,2,3-trimethylimidazolinium benzoate is obtained in a yield of 98%. As a result of an analysis of the target product through liquid chromatography, it is found that the purity is 99.5% or higher. The structure of the product is identified by elemental analysis, $^1$H-NMR and $^{13}$C-NMR.

EXAMPLE 6

The procedure of Example 4 is conducted except that 1,2,4-trimethylimidazoline is used instead of 1-ethyl-2-methylimidazoline. The results of the quaternizing reaction are shown in Table 1. The target 1,2,3,4-tetramethylimidazolinium benzoate is obtained in a yield of 98%. As a result of an analysis of the target product by liquid chromatography, it is found that the purity is 99.5% or higher. The structure of the product is identified by elemental analysis, $^1$H-NMR and $^{13}$C-NMR.

COMPARATIVE EXAMPLE 1

Figure 3:
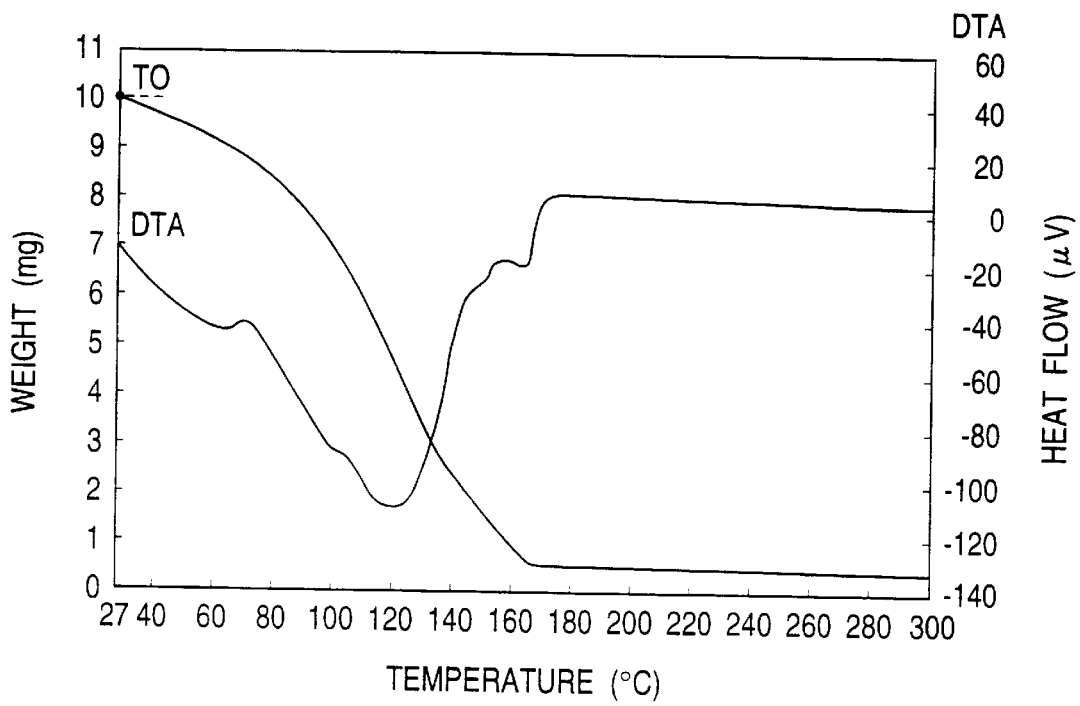
FIG. 3 illustrates the results of thermogravity-differential thermal analysis of a 1-ethyl-2,3-dimethylimidazolinium methyl carbonate mixture containing methanol.
Figure 4:
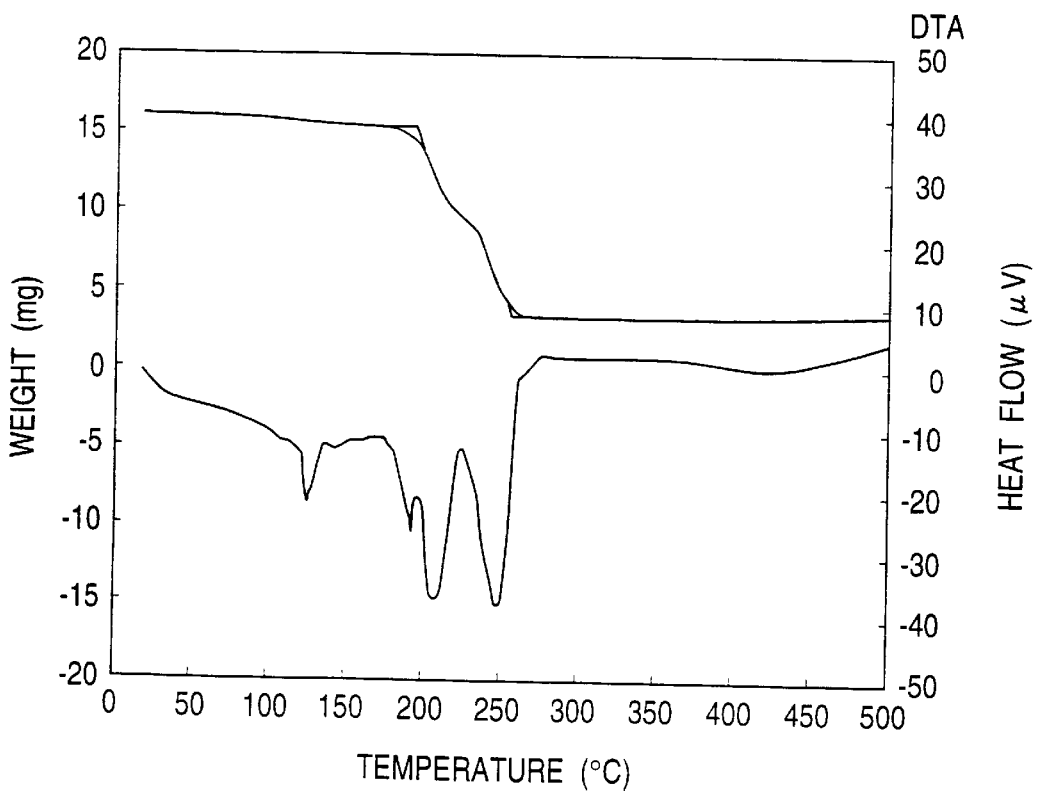
FIG. 4 illustrates the results of thermogravity-differential thermal analysis of tetramethylammonium methyl carbonate.

After the quaternizing reaction in Example 1, isolation of 1-ethyl-2,3-dimethylimidazolinium methyl carbonate is attempted by distilling off methanol and dimethyl carbonate from the reaction mixture under reduced pressure at room temperature. Instead of isolation, decomposition occurred. In FIG. 3, thermal analysis results of the 1-ethyl-2,3-dimethylimidazolinium methyl carbonate mixture containing methanol are shown, but evaporation of methanol occurred accompanied with the decomposition. By contrast, the conventional tetramethylammonium methyl carbonate is stable up to about 200° C. (FIG. 4), which permits isolation.

COMPARATIVE EXAMPLE 2

The procedure of Example 1 is conducted except that the water content in the reaction mixture is changed to 5 wt. %. From the beginning of the reaction, the reaction pressure shows a drastic increase owing to the abnormal emission of carbon dioxide gas. The reaction is terminated two hours after the pressure reached 20 kg/cm$^2$. The results of the quaternizing reaction are shown in Table 1. Side reactions substantially prevent the formation of 1-ethyl-2,3-dimethylimidazolinium methyl carbonate, which make it impossible to carry out the reaction with phthalic acid.

COMPARATIVE EXAMPLE 3

Into a 100-ml autoclave, 16.8 g (0.15 mole) of 1-ethyl-2-methylimidazoline and 27.0 g (0.30 mole) of dimethyl carbonate are charged. (In this case, excess dimethyl carbonate also serves as a solvent). By a Karl Fischer determination, the water content in the system is 160 ppm. The autoclave is heated for about 30 minutes to 130° C., at which temperature the reactants react. The reaction pressure shows an increase because of the abnormal emission of carbon dioxide gas so that the reaction is terminated 5 hours after the pressure reaches 20 kg/cm$^2$. As a result of an analysis of the reaction mixture by liquid chromatography, it is found that the conversion ratio of 1-ethyl-2-methylimidazoline is 100% but the yield of 1-ethyl-2,3-dimethylimidazolinium methyl carbonate is 39%. Such a very low yield prevents the execution of the reaction with phthalic acid.

COMPARATIVE EXAMPLES 4–7

The procedure of Example 1 is conducted except that 0.60 mole of toluene (Comparative Example 4), tetrahydrofuran (Comparative Example 5), ethanol (Comparative Example 6) and isopropanol (Comparative Example 7) are used as solvents instead of methanol, during the quaternization reactions. The results of the quaternizing reaction are shown in Table 1, from which it is found that the conversion ratio of 1-ethyl-2-methylimidazoline and yield of 1-ethyl-2,3-dimethylimidazolinium methyl carbonate in each reaction are very low.

To each of the reaction mixtures, 24.9 g (0.15 mole) of phthalic acid are added and methanol and dimethyl carbonate are distilled off under reduced pressure, and a solid is obtained. As a result of an analysis of the solid by liquid chromatography, the solid is found to contain a tertiary salt of unreacted 1-ethyl-2-methylimidazoline and phthalic acid and a number of unknown impurities. That is, the reaction product is only 1-ethyl-2,3-dimethylimidazolinium hydrogen phthalate having a very low purity (purity: about 60% or lower).

COMPARATIVE EXAMPLE 8

After the quaternizing reaction in Example 1, dimethyl carbonate is distilled off from the reaction mixture under reduced pressure, and a 1-ethyl-2,3-dimethylimidazolinium methyl carbonate mixture containing methanol is obtained. Water solvent is added to the mixture, followed by the addition of phthalic acid. The hydrolysis of 1-ethyl-2,3-dimethylimidazolinium methyl carbonate, however, occurs and no target product is obtained.

COMPARATIVE EXAMPLE 9

After the quaternizing reaction in Example 1, water solvent is added to the reaction mixture, followed by the addition of phthalic acid.

Hydrolysis of 1-ethyl-2,3-dimethylimidazolinium methyl carbonate, however, occurred and no target product is obtained.

The results are shown in Table 1.

TABLE 1

| Ex. | Solvent | Reaction temperature (°C.) | Reaction time (hr) | Reaction pressure (kg/cm$^2$) | Conversion ratio (%) | Yield (%) | Selectivity (%) |
|---|---|---|---|---|---|---|---|
| Ex. 1 | Methanol | 135 | 7 | 6–7 | 100 | 98 | 98 |
| Ex. 2 | Methanol | 135 | 7 | 6–7 | 100 | 98 | 98 |
| Ex. 3 | Methanol | 135 | 7 | 6–7 | 100 | 98 | 98 |
| Ex. 4 | Methanol | 145 | 7 | 8–10 | 100 | 98 | 98 |
| Comp. Ex. 2 | Methanol + water (5%) | 135 | 2 | 12–20 | 73 | 7 | 10 |
| Comp. Ex. 3 | Dimethyl carbonate | 130 | 5 | 7–20 | 100 | 39 | 39 |
| Comp. Ex. 4 | Toluene | 135 | 7 | 2–17 | 86 | 52 | 61 |
| Comp. Ex. 5 | Tetrahydrofuran | 135 | 7 | 4–17 | 53 | 15 | 29 |
| Comp. Ex. 6 | Ethanol | 135 | 7 | 4–7 | 78 | 62 | 79 |
| Comp. Ex. 7 | Isopropanol | 135 | 7 | 7–10 | 77 | 60 | 78 |

While the invention has been described in detail and with reference to specific examples thereof, it will be apparent to one skilled in the art that various changes and modifications can be made therein without departing from the spirit and scope thereof.

What is claimed as new and desired to be secured by letters patent of the United States is:

1. A process for the preparation of an N-alkyl-N'-methylimidazolinium salt of an organic acid, which comprises:
   a) preparing a quaternization product of an N-alkyl-N'-methylimidazolinium methyl carbonate by methylating a N-alkylimidazoline with dimethyl carbonate, and then
   b) reacting a resulting N-alkyl-N'-methylimidazolinium methyl carbonate, in an anion exchange reaction, with an organic acid,
   wherein each of steps a) and b) is conducted in methanol as a solvent, and
   wherein the amount of dimethyl carbonate per mol of N-alkylimidazoline ranges from about 1 to 5 mols, the amount of methanol solvent ranges from 1 to 20 mols per mol of N-alkylimidazoline, and
   wherein said step a) of said process is effected at a temperature in the range of about 110° to 170° Cm and under a pressure of from about 5 to 20 atmospheres.

2. The process of claim 1, wherein the water content in the reaction system is maintained at less than 1 wt % in both steps a) and b).

3. The process of claim 1, wherein the reaction mixture obtained in step a) is used as is and step b).

4. The process of claim 1, wherein the N-alkylimidazoline reactant in step a) is a compound having the formula (I):

wherein R' represents a $C_{1-4}$ alkyl group, $R^2$ represents a $C_{1-19}$ alkyl group or a hydrogen atom, and $R^3$ and $R^4$ each independently represent a methyl group, ethyl group or hydrogen atom.

5. The process of claim 3, wherein N-alkylimidazoline is at least one compound selected from the group consisting of 1-methylimidazoline, 1 ethylimidazoline, 1,2-dimethylimidazoline, 1-ethyl-2-methylimidazoline, 1,2,4-trimethylimidazoline, 1-ethyl-2,4-dimethylimidazoline and 1,4-dimethyl-2-ethylimidazoline.

6. The process of claim 1, wherein the organic acid used in step b) is phthalic acid or benzoic acid.

7. The process of claim 5, wherein said amount of dimethyl carbonate ranges from 1 to 2 mols.

8. The process of claim 6, wherein said amount of dimethyl carbonate ranges from 1.3 to 1.7 mols.

9. The process of claim 1, wherein said amount of methanol solvent ranges from 2 to 10 mols.

10. The process of claim 9, wherein said amount of methanol solvent ranges from 3 to 7 mols.

11. The process of claim 1, wherein the reaction temperature is from about 130° to 150° C.

12. The process of claim 1, wherein said organic acid is selected from the group consisting of carboxylic acid, sulfonic acid, alkyl phosphate and phenol.

13. The process of claim 1, wherein a water content thereof is less than 1 wt %, based on the total weight.

14. The process of claim 1, wherein step b) is effected at a temperature of about 10° to 100° C.

15. The process of claim 14, wherein step b) is effected at a temperature of about 20° to 60° C.

* * * * *